US005785664A

United States Patent [19]

Rosenberg

[11] Patent Number: 5,785,664

[45] Date of Patent: Jul. 28, 1998

[54] APPARATUS AND METHOD FOR THE DIAGNOSIS OF TRUE LABOR

[75] Inventor: Ethan Rosenberg, Monsey, N.Y.

[73] Assignee: Hygeia Biomedical Research Inc., Monsey, N.Y.

[21] Appl. No.: 585,790

[22] Filed: Jan. 16, 1996

[51] Int. Cl.$^{6}$ .................... A61B 5/103

[52] U.S. Cl. .................... 600/588; 600/551

[58] Field of Search .................... 128/775, 774, 128/738, 733, 734, 782, 778, 904

[56] References Cited

U.S. PATENT DOCUMENTS

| | | | |
|---|---|---|---|
| 4,256,118 | 3/1981 | Nagel | 128/733 |
| 4,719,925 | 1/1988 | Persons | 128/733 |
| 4,967,761 | 11/1990 | Nathanielsz | 128/733 |
| 5,042,503 | 8/1991 | Torok et al. | 128/775 |
| 5,301,680 | 4/1994 | Rosenberg | 128/733 |

FOREIGN PATENT DOCUMENTS

| | | |
|---|---|---|
| 0 306 915 A1 | 3/1989 | European Pat. Off. . |
| 37 29 760 A1 | 3/1989 | Germany . |
| WO 95/31932 | 11/1995 | WIPO . |

OTHER PUBLICATIONS

"External Recording and Processing of Fast Electrical Activity of the Uterus in Human Parturition" by J.G. Planes et al., Med. & Bio Eng. & Comput., 1984, 22 pp. 585–591.

"Electromyographic Observations on the Human Uterus during Labor" by G.M. J. A. Wolfs and M. van Leeuwen, Acta Obstetricia et Gynecol. Scand. Suppl, 90, 1979.

"The Electrical Potentials Of the Human Uterus in Labor", Dill and Maiden, Amer. Jour. Obstetrics and Synecol. pp. 735–745 No. 52 735 (1946).

"Human Abdominal EHG Processing For Uterine Contraction Monitoring", C. Marque & J Duchene, Applied Biosensors, D.L. Wise E., Butterworth Publisher, Boston 187–226, 1989.

"Uterine EHG Processing Obstetrical Monitoring", by C. Marque, et al., IEEE Transactions on Bio. Eng. vol. 33, No. 12, Dec. 1986, pp. 1182–1187.

"Surveilance Obstetricale Utilisant Le Signal Electromyographique Uterin" S. Planque, C. Marque, J. Duchene, Div. Biomecanique et Instrumentation Medicale, 1989, pp. 993–996.

"Instrument For Measuring the Contractile Activity of the Uterus" V.F. Pronin, Biomedical Engineering vol. 7, No. 4, pp. 212–215 Jul. 1973.

"Obstetrical Monitoring Device Using Uterine EMG Analysis" by Marque, C. and Duchene, J. , IEEE Engineering in Med. & Bio. Society 10th Annual Inter. Confer. vol. 12, No. 2, 1990.

(List continued on next page.)

*Primary Examiner*—Max Hindenburg
*Assistant Examiner*—Pamela L. Wingood
*Attorney, Agent, or Firm*—Perman & Green, LLP

[57] ABSTRACT

Disclosed are systems and methods for detecting an onset of true labor in a pregnant mammal. In accordance with a method of this invention the following steps are executed: (a) detected electrical signals from a succession of muscular contractions associated with labor; (b) determining a spectral content of the electrical signals for each contraction; (c) determining a discriminant (δ) from the determined spectral content for each contraction so as to provide a set of discriminants, individual ones of the set of discriminants being associated with an individual one of the contractions; and (d) indicating a beginning of true labor when a slope of at least two discriminants of the set of discriminants exceeds a first threshold value and when a magnitude of a last determined discriminant exceeds a second threshold value. The onset of true labor can also be indicated when a value of a critical determinant exceeds a threshold value, the value of the critical determinant being obtained from a combination of the slope of at least two discriminants of the set of discriminants and a magnitude of a last determined discriminant.

30 Claims, 6 Drawing Sheets

DISPLAY 2

+10
Y
δ
X
T
−10

OTHER PUBLICATIONS

"First Results On Uterine EMG Monitoring During Pregnancy," Gondry et al. IEEE 14th Annual Conf. Paris, vol. 14, 1992, pp. 2609–2610.

"Uterine EMG: Experimental and Mathematical Determination of the Relationship Between Internal and External Recordings", IEEE Annual Conf. Orlando, vol. 13, 1991, pp. 485–486. by S. Mansour, et al.

Abstract of J. Duchene et al. First European Conference on Biome. Engineering, Nice, France, February 17–20, 1991.

Abstract at XIVth Congress of the International Primatological Society Strasbourg, France, Aug. 16–21, 1992, by Guy Germain.

"Uterine EMG Processing For Labor Monitoring" by Marque C. & Duchene, J., Innov. Tech. Biol. Med.; vol. 10, No. 1, 1989, pp. 14–23.

"Electrical Activity of the Human Uterus In Labor", Charles Steer, M.D. and G. Hertsch, Am. Jour. of Obstetrics and Gynecology, vol. 59, Jan. 1950, pps. 25–40.

Electrohysterography during Pregnancy: Gondry et al., Biomedical Instrumentation & Technology 1993 pp. 318–324.

"Uterine electromyography: A critical review" Devedeux et al., Am.J.Obstet. & Gynecol. 1993 vol. 169, No. 6, pp. 1636–1653.

"An Optimal Set of Discriminant Vectros" D. Foley and J. Sammon, Jr., IEEE Transactions On Computers, Mar. 1975, vol. C24, No. 3, pp. 218–289.

ELECTRODES
1
2
A/D
3
FILTER
5
ENVELOPE DETECTOR
4
$t_1$ $t_2$
27
MEMORY 1
7
PSD/FT
8
ADD
9
∫f(x)
25
CALC. δ
26
MEMORY 2
11
COMPA-RATOR
13
DISPLAY 3
14
MEMORY 3
20
XMTR
21
22
PRACTITIONER'S CONSOLE
30
ENABLE XMTR
13a
LOM,34'

APPARATUS AND METHOD FOR THE DIAGNOSIS OF TRUE LABOR

FIELD OF THE INVENTION

This invention relates generally to medical and veterinary instrumentation and, in particular, to medical and veterinary instrumentation for use in diagnosing premature labor.

BACKGROUND OF THE INVENTION

The risks to babies born prematurely are great and the economic costs to society continue to increase. At present, infants less than 22 weeks gestation are not predicted to survive, and at 28 weeks, only 77% survive. The total yearly cost for preterm babies in the U.S. is in excess of five billion dollars. In order for preterm babies to have a better chance of survival, premature labor must be detected prior to any dilation of the cervix, so that effective drug therapy can be instituted.

In more than 50% of cases of threatened premature labor, the patient's contractions are those of false labor and will stop spontaneously. However, when the patient calls her physician, she will be advised to go to the hospital. If, when the patient arrives at the hospital, her cervix is not significantly dilated, she will be observed for a period of time. If the contractions stop, the patient will be sent home. If, however, they continue, the cervix can dilate further and either make it more difficult to stop the labor, or make the birth of the baby inevitable. The drugs used to stop contractions of premature labor pose a significant risk, both to the mother and baby. Before a physician will start administering these drugs, he must be absolutely sure that the patient is in true labor.

Every muscle produces an electric signal when it contracts. The electric signal from the heart can be measured as an electrocardiogram (EKG), and from the uterus as an electrohysterogram (EHG). This EHG will vary during pregnancy and labor.

In my U.S. Pat. No. 5,301,680, issued Apr. 12, 1994, entitled "Apparatus and Method for the Diagnosis of Labor", there are described systems and methods that determine a periodicity of an electrical signal in an abdominal region. A uterine contraction vector having a magnitude and propagation direction is then determined and is employed to distinguish true labor from false labor, and to detect the onset of true labor. Methods and apparatus are also disclosed for determining the extent of cervical dilation.

It is known to those skilled in the art that, as labor progresses, there is a shift toward higher frequencies in the frequency spectrum of the electrical activity of the uterus.

By example, Marque and Duchene ("Human Abdominal EHG Processing for Uterine Contraction Monitoring", in *Applied Biosensors*, D. L. Wise Ed., Butterworth Publisher, Boston, 187–226 (1989)), have disclosed a technique for the detection of premature labor by calculating a criterion. The criterion is based on the energy in a total band (0.2–3.0 Hz), a low frequency band (0.2–0.45 Hz), a high frequency band (0.8–3.0 Hz), and the length of a recorded EHG burst. These authors calculate and graph this criterion during contractions, and show that if it remains negative it is an "effective" contraction, and if it becomes positive it is an "ineffective" contraction.

SUMMARY AND OBJECTS OF THE INVENTION

The inventor has discovered that more meaningful diagnostic information can be obtained from the electrical activity of the uterus, by calculating a parameter representative of each entire uterine contraction, and by measuring a change in this parameter with respect to parameters calculated from subsequent contractions.

It is thus one object of this invention to provide a method, and an apparatus for accomplishing this method, whereby true labor is distinguished from false labor, by measuring the duration of the electrical activity and by measuring the energy in the uterine electrical activity, and by determining a parameter characteristic of these measurements.

It is a further object of this invention to predict the onset of true labor by measuring a temporal change in the determined parameter.

It is another object of this invention to provide an apparatus which may be worn by a pregnant mammal which will signal the onset of true labor.

A still further object of the invention provides instrumentation for remotely monitoring a pregnant mammal to aid in diagnosing true labor from false labor.

The foregoing and other problems are overcome, and objects of the invention are realized, by methods and apparatus utilizing an electromyographic detection of electrical fields inherent in muscular activity for the diagnosis of premature labor. The apparatus includes a system for measuring the duration and spectral characteristics, such as by a Fourier transform or power spectrum, of the electrical signal in the abdominal region and for processing said measurements to indicate and predict the onset of true labor. The system senses electrical activity indicating a smooth muscle contraction, such as a uterine contraction, and calculates the duration of the electrical activity and its Fourier transform or its power spectrum.

More specifically, the Fourier transform or the power spectrum is integrated in a plurality of frequency ranges. Additionally, the electrical activity may be displayed to a practitioner, and/or recorded and stored for subsequent analysis.

In one aspect the invention teaches (a) the detection of the electrical activity of the uterus, and the determination of a parameter inherent in the determined Fourier transform or power spectrum and also the determination of the duration of the electrical activity; (b) the display of the value of this parameter and its change with respect to time; and (c) the display of the result of the calculations so as to provide diagnostic information. Further, in accordance with the teaching of the invention, (d) an indication is displayed if the results of the above determinations indicate the onset of true labor.

This invention furthermore teaches the remote monitoring of a pregnant mammal, in combination with the methods and apparatus for enabling a practitioner to remotely make a diagnosis so as to distinguish true labor from false labor.

By automatically analyzing the EHG obtained from a pregnant mammal, this invention detects differences in the signals and enables a discrimination to be made between false labor contractions (Braxton-Hicks) and true labor contractions.

In accordance with a method of this invention for detecting an onset of true labor in a pregnant mammal, and a system for accomplishing the method, the following steps are executed: (a) detecting electrical signals from a succession of muscular contractions associated with labor; (b) determining a spectral content of the electrical signals for each contraction; (c) determining a discriminant ($\delta$) from the determined spectral content for each contraction so as to provide a set of discriminants, individual ones of the set of discriminants being associated with an individual one of the contractions; and (d) indicating a beginning of true labor when a slope of at least two discriminants of the set of discriminants exceeds a first threshold value and when a magnitude of a last determined discriminant exceeds a second threshold value.

The step of detecting includes the steps of digitizing the electrical signals and filtering the digitized electrical signals, and the step of determining a spectral content includes a step of performing a discrete Fourier transform calculation on the digitized electrical signals, or a step of performing a power spectral density calculation on the digitized electrical signals.

The step of detecting includes a step of operating an envelope detector for detecting a time (t1) that each contraction begins and a time that each contraction terminates (t2).

The step of determining a discriminant employs the expression:

$$\delta=\rho H_\alpha+\sigma H_\beta+\tau H_\gamma+\phi H_\epsilon,$$

where $H_\alpha$, $H_\beta$, $H_\gamma$ and $H_\epsilon$ represent the spectral energy in a plurality of different frequency ranges, and where $\rho$, $\sigma$, $\tau$ and $\phi$ are constants selected so that $\delta$ has a negative value for false labor contractions, and a positive value for true labor contractions. In a presently preferred embodiment of this invention the plurality of different frequency ranges are within a band of frequencies from about 0.1 Hz to about 5.0 Hz.

The method further includes the steps of digitizing and storing the detected electrical signals; and the step of indicating includes a further step of transmitting at least the stored, digitized electrical signals to a remote location.

In a further embodiment of this invention, the step of indicating a beginning of true labor is accomplished when a value of a critical determinant exceeds a threshold value, the value of the critical determinant being obtained from a combination of the slope of at least two discriminants of the set of discriminants and a magnitude of a last determined discriminant.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

The disclosure of my above-mentioned U.S. Pat. No. 5,301,680, issued Apr. 12, 1994, entitled "Apparatus and Method for the Diagnosis of Labor", is incorporated by reference herein in its entirety.

As employed herein, the term "pregnant mammal" is not intended to be limited to only a pregnant human female, in that the methods and apparatus of this invention may be utilized by both medical and veterinary practitioners.

Also, as employed herein, the term "diagnostic information" is intended to refer to data and/or signals (audible and/or visible) emanating from the apparatus of the invention, the data and/or signals being the result of the processing by the apparatus, in accordance with the methods of the invention, of the voltages detected by suitable transducers, such as but not limited to electrodes, that are attached to a pregnant mammal. These voltages may be detected and then processed in close proximity to the pregnant mammal, or may be transmitted over a suitable telemetry or communications link and processed remotely from the pregnant mammal. Furthermore, the data and/or signals are presented to a practitioner in such a manner so as to aid the practitioner in at least distinguishing true from false labor. The data and/or signals are additionally presented to a practitioner in such a manner so as to aid the practitioner in determining and predicting the onset of true labor.

Figure 1A:
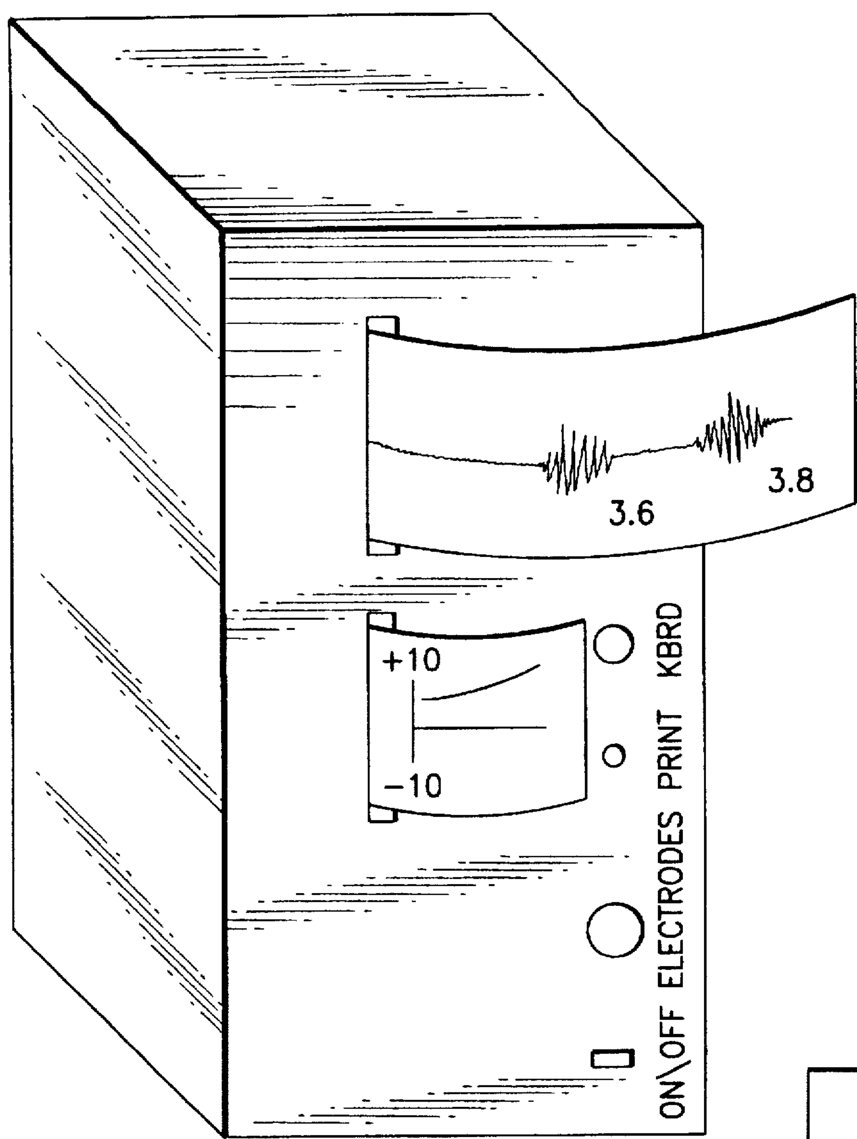
FIG. 1A is a pictorial representation of a Labor Onset Monitor (LOM) that is constructed and operated in accordance with the invention.
Figure 1B:
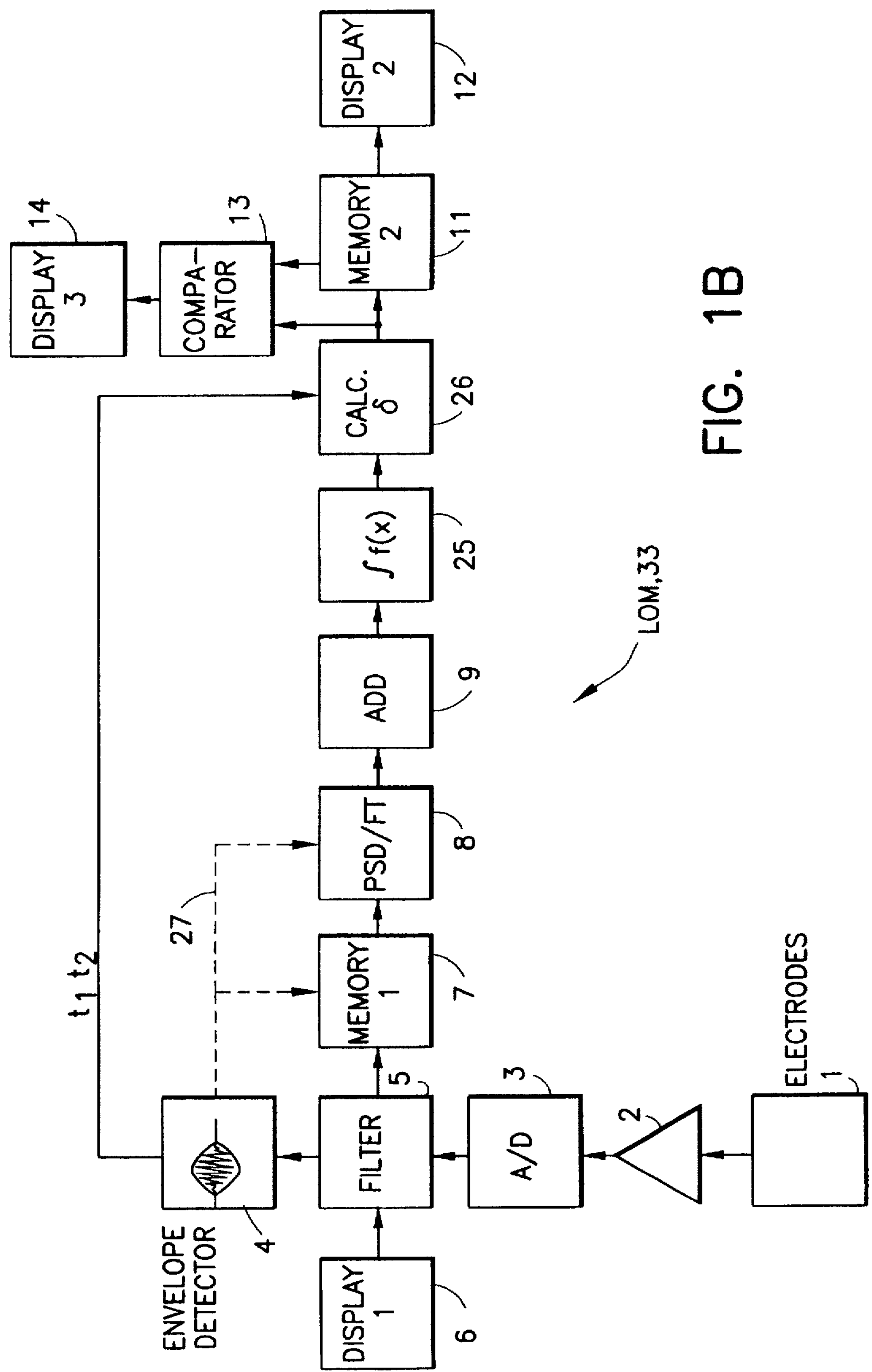
FIG. 1B is a block circuit diagram of a Labor Onset Monitor that is constructed and operated in accordance with the invention.

FIGS. 1A and 1B illustrate the Labor Onset Monitor (LOM) 33 that is constructed and operated in accordance with the invention. The LOM 33 includes a set of electrodes 1. The electrodes 1 may be EKG or equivalent electrodes, or may be capacitively coupled electrodes of type described by W. H. Ko and J. Hynecek in "Dry Electrodes and Electrode Amplifiers", *Biomedical Electrode Technology-Theory and Practice*, pgs. 169–181, ed. Miller, H. A. and Harrison, D. C., Academic Press, New York (1974). In general, any suitable transducer for detecting electrical energy can be employed.

The set of electrodes 1 are positioned on the abdomen of the pregnant mammal, midway between the fundus and the symphysis pubis, at an inter-electrode spacing of from approximately 1 to 7 cm. A ground electrode is positioned on a part of the body remote from the abdomen; e.g., the thigh. The electrodes 1 are connected to a differential amplifier 2, with the following typical characteristics:

CMRR>100 dB

Gain 50,000

Input Impedance>1,000 MegOhms

Figure 2:
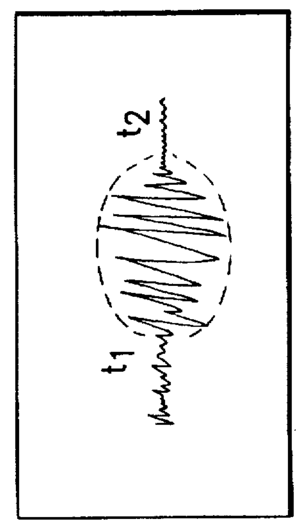
FIG. 2 illustrates a first display (Display1) of typical waveforms of the uterine electromyogram as detected by the electrodes that are coupled to the system of FIG. 1B.

The amplified electrode signal is converted to digital form with an analog to digital (A/D) converter 3, at an A/D sampling rate in a range of 8 to 256 conversions per second. The digitized signal is digitally filtered by a filter 5 in a selected frequency range; e.g. 0.1 to 5.0 Hz, and may be displayed on an appropriate display device 6, (Display1, FIG. 2), such as a conventional CRT, and also stored in a storage device 7, such as semiconductor memory and/or a conventional fixed or removable disk.

The presence of electrical activity from the uterus is detected by an envelope detector 4, which determines and stores the time (t1) of the start of the electrical activity, and which also determines and stores the end of the electrical activity (t2). The envelop detector 4 activates a control loop 27, which causes the storage device 7 to initiate an incremental transfer of the currently acquired data to a Fourier transform (FT) or Power Spectral Density (PSD) module 8. This incremental transfer continues until the envelop detector 4 senses the end of the contraction at t2, at which time the envelop detector 4 deactivates the control loop 27.

A Fourier transform or a Power Spectral Density 8 is then incrementally calculated for the filtered signal, and the incremental calculations are summed in a summation device 9. A suitable embodiment for the FT/PSD block 8 is discussed below. The FT or PSD is integrated, by an integration module 25, in a plurality of selected frequency ranges; e.g., $\alpha$, $\beta$, $\gamma$ and $\epsilon$, selected from the range of filtering, to give the energy in the ranges $H_\alpha$, $H_\beta$, $H_\gamma$ and $H_\epsilon$, respectively. Suitable, but not limiting, frequency ranges are as follows: $\alpha$=0.1–1.25 Hz; $\beta$=1.25–2.5 Hz; $\gamma$=2.5–3.75 Hz; and $\epsilon$=3.75–5 Hz. The duration, $\lambda$=t2–t1, of the electrical activity is obtained from the envelope detector 4.

Next, a discriminant $\delta$ for the electrical activity is determined, in a calculation module 26, from a combination of the energies, as for example:

$$\delta=\rho H_\alpha+\sigma H_\beta+\tau H_\gamma+\phi H_\epsilon$$

where constants $\rho$, $\sigma$, $\tau$ and $\phi$ are selected so that $\delta$ has a negative value for false labor contractions, and a positive value for true labor contractions. This is preferably accomplished by taking measurements from a representative sample of pregnant mammals, and thus establishing the values of the constants accordingly. The discriminant $\delta$ may, for example, range in value from −10 to +10. The value of $\delta$ is stored, along with the time T1 of the termination of the electrical activity, as an ordered pair (T1, $\delta_1$) in a storage device 11, and may also be displayed on a suitable display device 12 (Display2, FIG. 3A).

At the end of the next contraction, the slope $\Sigma$ of the two discriminants $\delta$ (i.e., the discriminant obtained for the contraction just ended (T2, $\delta_2$) and the discriminant from the preceding contraction (T1, $\delta_1$) is calculated as:

$$\Sigma=(\delta_2-\delta_1)/(T_2-T_1).$$

That is, the change in the discriminant $\delta$ is determined between two successive contractions. Alternatively, a plurality of the ordered pairs (Tn, $\delta_n$) can be accumulated for a plurality of successive contractions, and the slope determined over the plurality of ordered pairs.

If the value of the slope $\Sigma$ exceeds a critical (c) value $\Sigma_c$, and if $\delta$ exceeds a critical (c) value $\delta_c$, as determined by a comparator 13, an audible and/or visual warning signal is given using the display device 14 (Display3, FIG. 3B) to indicate the onset of true labor. Otherwise, the output of the comparator 13 is employed to display a "normal" signal on the display device 14, indicating that true labor has not begun.

Figure 3A:
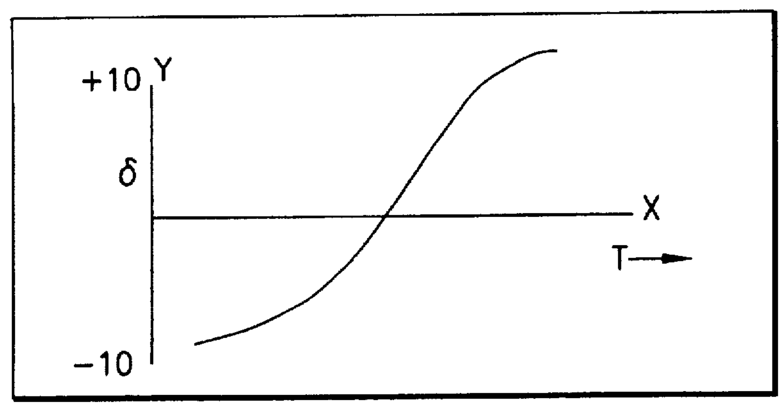
FIG. 3A illustrates a second display (Display2) showing a change in a discriminant ($\delta$) parameter as a function of time.
Figure 3B:
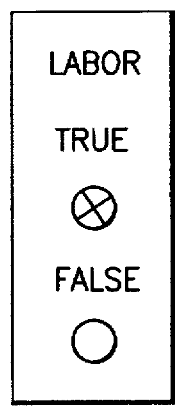
FIG. 3B is an example of a display (Display3) that is responsive to the change in the $\delta$ parameter as a function of time, as detected by the embodiments of FIGS. 1B, 4B, 5 and 6, for indicating a false or a true labor condition.

By example, and referring to FIG. 3A, the critical values may be established such that the onset of true labor is indicated when the discriminant line passes, with a predetermined positive slope, through a range of discriminant values located on or near the x-axis.

It is also within the scope of the teaching of this invention to employ a combination (e.g., a linear combination) of $\Sigma$ and $\delta$ to obtain a value of a critical determinant. When the value of the critical determinant is determined to exceed a threshold value, the onset of true labor is indicated.

Figure 4A:
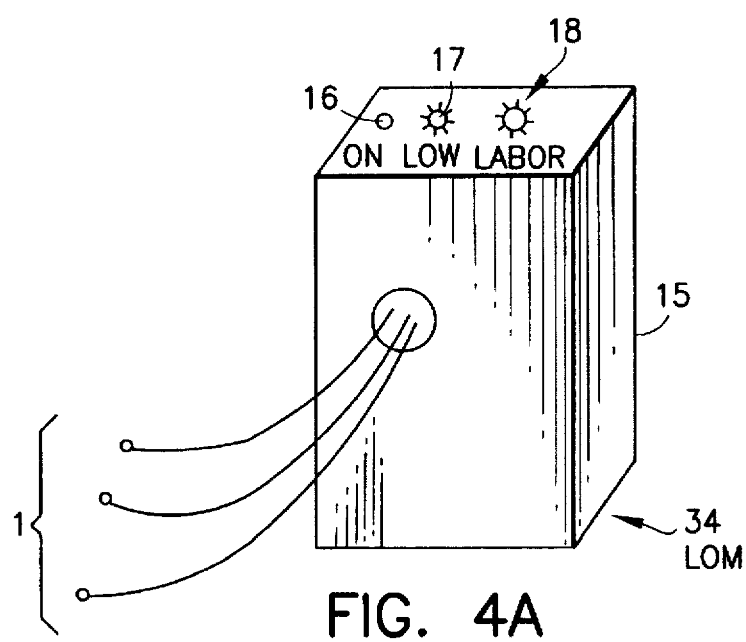
FIG. 4A is a pictorial representation of a second embodiment of the invention which is designed to be worn by a pregnant mammal.
Figure 4B:
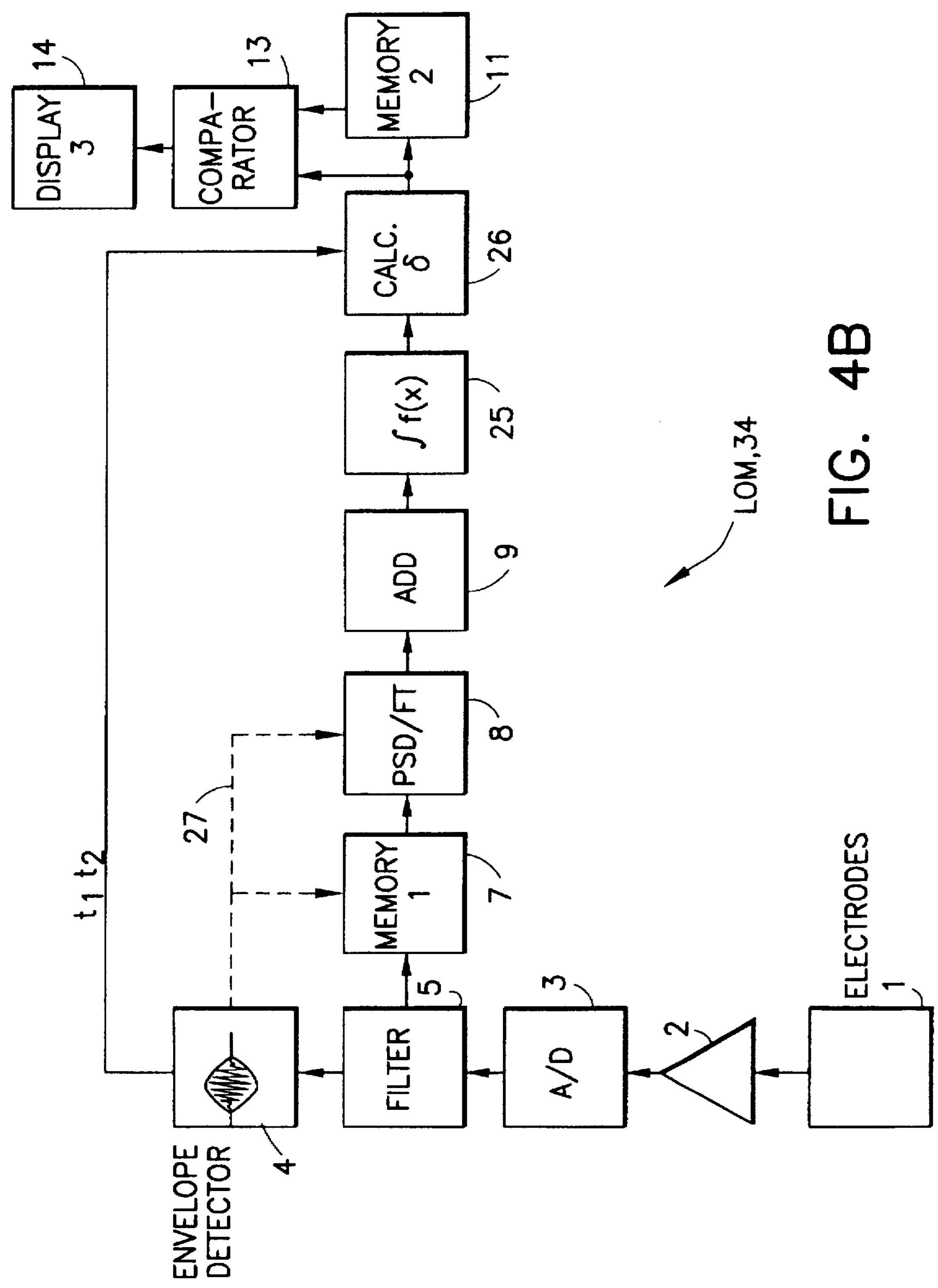
FIG. 4B is a block circuit diagram of a second embodiment of the invention which is designed to be worn by a pregnant mammal.

A further embodiment of the LOM (designated 34) is shown in FIGS. 4A and 4B. The operation of this embodiment is similar to that as described for the embodiment as shown in FIG. 1, except for the absence of the display devices 6 and 12. This embodiment is intended to be carried on, by, or in close proximity to the pregnant mammal within a suitable battery-powered electronics enclosure 15. In this embodiment of the invention, when the comparator 13 senses the onset of true labor an audible and/or visual signal is given.

A pictorial representation of the embodiment described in FIG. 4B is shown in FIG. 4A. This representation depicts the electronics enclosure 15, electrodes 1 and associated wiring and connectors, an ON/OFF indicator 16, a low battery indicator 17, and the labor warning signal 18. That is, in this embodiment the Display3 is embodied in the labor indicator 18.

Figure 5:
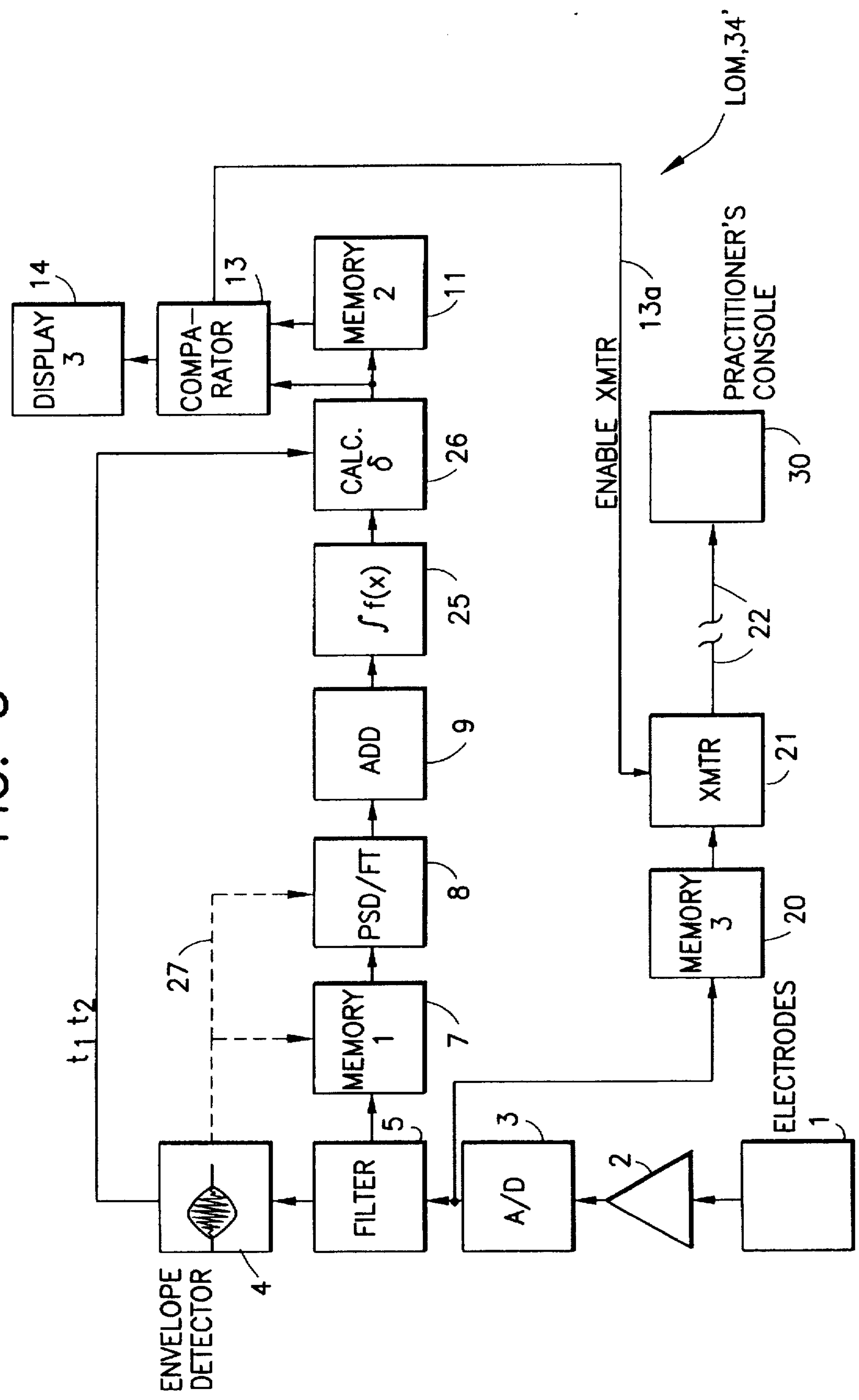
FIG. 5 is a block circuit diagram of a third embodiment of the invention which is designed to be worn by a pregnant mammal, that provides for remotely monitoring the pregnant mammal over a communications link.

A further embodiment of the LOM, designated as 34', is shown in FIG. 5. This embodiment is intended to enable the remote monitoring of a pregnant mammal via a communications link. In this embodiment of the invention, the output of the A/D converter 3 is stored in a storage device 20. When the comparator 13 senses the start of true labor, a signal is sent via a control link 13*a* to a transmitter 21. The transmitter 21 accesses the storage device 20 and transmits the data contained therein via a telemetry link 22 to a practitioner's console 30. The telemetry link 22 can be any suitable data transmission means, such as an RF link, a telecommunications link, and a data link.

Figure 6:
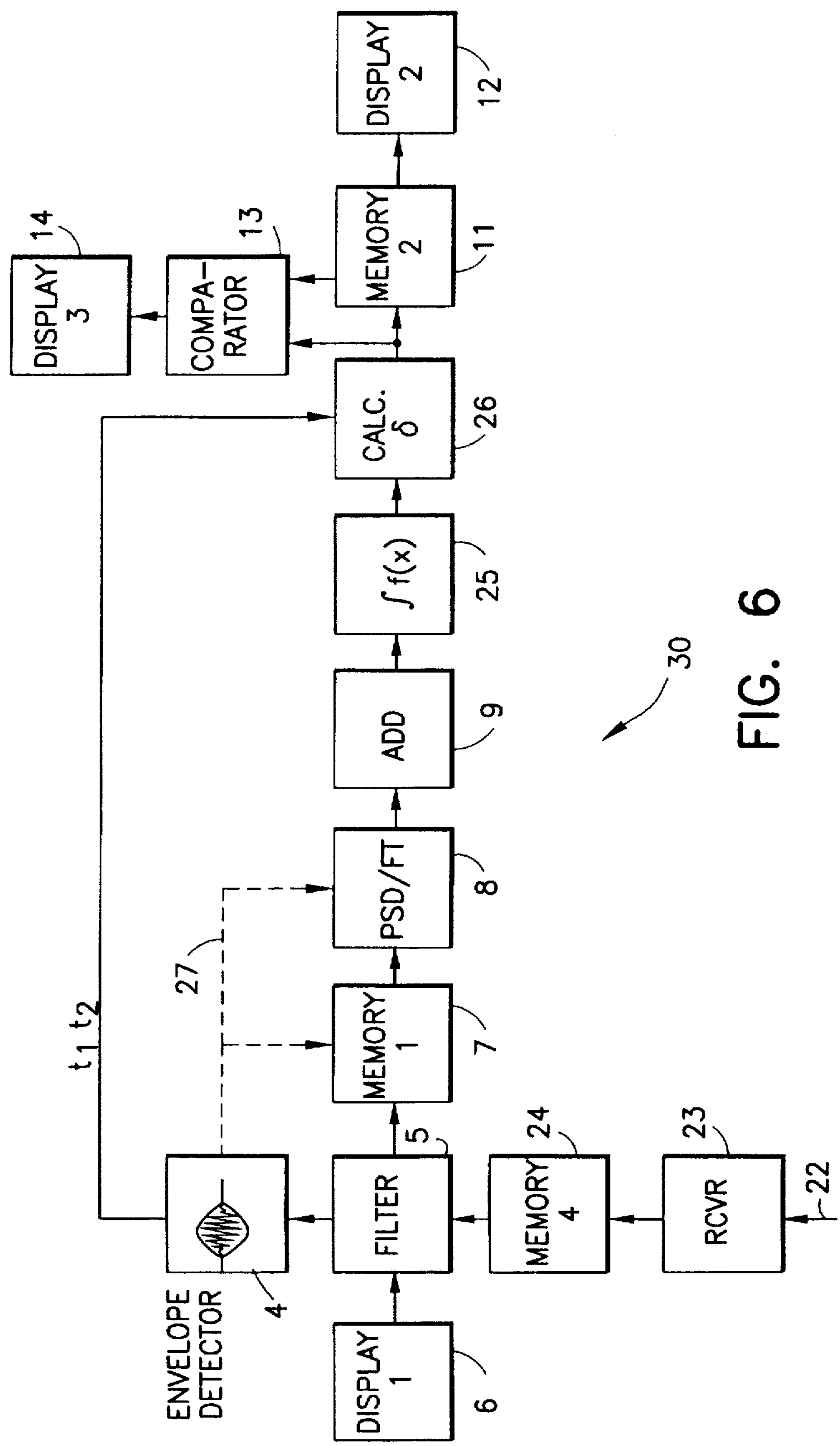
FIG. 6 is a block circuit diagram of a embodiment of a practitioner's console that forms a portion of the labor onset monitor system shown in FIG. 5.

FIG. 6 is a block circuit diagram of the practitioner's console 30. A receiver 23 receives the data from the telemetry link 22 and stores the received data in a storage device 24. The data is then replayed, at high speed, into the envelope detector 4, and is subsequently processed as described with regard to FIG. 1B.

Alternatively, and referring again to FIG. 5, in the LOM 34', the input to the transmitter is coupled instead to the storage device 7, or to the storage device 11, thereby simplifying the construction of the practitioners console 30. That is, in these other embodiments the practitioner's console 30 relies on the processing of the contraction-related signals that is performed by the LOM 34'. In these other embodiments it may still be desirable to provide the storage device 20, and to also transmit the "raw" A/D converter data from the storage device 20 to the practitioner's console 30. In this manner the practitioner's console 30, is enabled to check the accuracy of the calculations performed by the LOM 34', and/or to employ other and/or more sophisticated calculations on the raw A/D converter data.

As was described above, it is preferred to calculate some form of the Fourier transform (e.g., a fast Fourier Transform, a discrete Fourier Transform, a Power Spectral Density (PSD)) in the block 8 of FIGS. 1B, 4B, and 5. In a presently preferred, but not limiting, embodiment of this invention the LOM employs a discrete Fourier transform (DFT) when processing the filtered spectral data obtained from the electrodes 1.

By example, one suitable software package for performing a discrete Fourier transform is available from National Instruments, and is described in a publication entitled "Fast Fourier Transforms and Power Spectra in Lab Windows®", Application Note 020, J. Pasquarette, National Instruments Corporation (August 1991). Furthermore, and as is described at page 10 of this publication, the software package includes a function named Spectrum that enables the power spectrum of a signal to be determined. Thus, the PSD blocks 8 of FIGS. 1B, 4B, 5 and 6 can also be implemented with this particular software package.

In more detail, the power spectrum, $S_{xx}$, of a time domain signal is defined by: $S_{xx}(k)=|X(k)|^2/n^2$, where $S_{xx}(k)$ is the discrete power spectrum of a discrete time domain signal x(i), X(k) is the discrete Fourier transform of x(i), and n is the number of data points.

Although described above in the context of discrete circuit elements such as envelope detectors, digital filters, etc., it should be appreciated that all or most of the illustrated blocks could be implemented with a suitably programmed data processor, such as a digital signal processor (DSP). In like manner the various separate memories could all be contained within a single memory device or medium. Thus, while the invention has been particularly shown and described with respect to presently preferred embodiments thereof, it will be understood by those skilled in the art that changes in form and details may be made therein without departing from the scope and spirit of the invention.

What is claimed is:

1. A method for detecting an onset of true labor in a pregnant mammal, comprising the steps of:

detecting electrical signals from a succession of muscular contractions associated with labor;

determining a spectral content of the electrical signals for each contraction;

determining a discriminant (δ) from the determined spectral content for each contraction so as to provide a set of discriminants, individual ones of the set of discriminants being associated with an individual one of the contractions; and indicating a beginning of true labor when a slope of at least two discriminants of the set of discriminants exceeds a first threshold value and when a magnitude of a last determined discriminant exceeds a second threshold value.

2. A method as set forth in claim 1, wherein the step of detecting includes the steps of digitizing the electrical signals and filtering the digitized electrical signals, and wherein the step of determining a spectral content includes a step of performing a Fourier transform calculation on the digitized electrical signals.

3. A method as set forth in claim 1, wherein the step of detecting includes the steps of digitizing the electrical signals and filtering the digitized electrical signals, and wherein the step of determining a spectral content includes a step of performing a power spectral density calculation on the digitized electrical signals.

4. A method as set forth in claim 1, wherein the step of detecting includes a step of detecting a time (t1) that each contraction begins and a time (t2) that each contraction terminates.

5. A method for detecting an onset of true labor in a pregnant mammal, comprising the steps of:

detecting electrical signals from a succession of muscular contractions associated with labor;

determining a spectral content of the electrical signals for each contraction;

determining a discriminant (δ) from the determined spectral content for each contraction so as to provide a set of discriminants, individual ones of the set of discriminants being associated with an individual one of the contractions; and indicating a beginning of true labor when a slope of at least two discriminants of the set of discriminants exceeds a first threshold value and when a magnitude of a last determined discriminant exceeds a second threshold value, wherein the step of determining a discriminant determines the discriminant in accordance with the expression:

$$\delta=\rho H_\alpha+\sigma H_\beta+\tau H_\gamma+\phi H_\epsilon,$$

where $H_\alpha$, $H_\beta$, $H_\gamma$ and $H_\epsilon$ represent the spectral energy in a plurality of different frequency ranges, and where ρ, σ, τ and φ are constants selected so that δ has a negative value for false labor contractions, and a positive value for true labor contractions.

6. A method as set forth in claim 5, wherein the plurality of different frequency ranges are within a band of frequencies from about 0.1 Hz to about 5.0 Hz.

7. A method as set forth in claim 6, wherein α=0.1–1.25 Hz; β=1.25–2.5 Hz; γ=2.5–3.75 Hz; and ε=3.75–5 Hz.

8. A method as set forth in claim 1, and further comprising the steps of:

digitizing the detected electrical signals; and storing the digitized electrical signals; and wherein the step of indicating includes a further step of;

transmitting at least the stored, digitized electrical signals to a remote location.

9. A method as set forth in claim 1, wherein the step of detecting includes the steps of digitizing the electrical signals and filtering the digitized electrical signals, and further comprising a step of displaying the filtered digitized electrical signals.

10. A method as set forth in claim 1, and further comprising a step of displaying at least one determined discriminant.

11. A method as set forth in claim 1, wherein the step of indicating includes a step of generating at least one of a visual and an aural indicator.

12. A system for detecting an onset of true labor in a pregnant mammal, comprising:

means for detecting electrical signals from a succession of muscular contractions associated with labor;

means for determining a spectral content of the electrical signals for each contraction;

means for determining a discriminant (δ) from the determined spectral content for each contraction so as to provide a set of discriminants, individual ones of the set of discriminants being associated with an individual one of the contractions; and means for indicating a beginning of true labor when a slope of at least two discriminants of the set of discriminants exceeds a first threshold value and when a magnitude of a last determined discriminant exceeds a second threshold value.

13. A system as set forth in claim 12, wherein said detecting means includes means for digitizing the electrical signals and means for filtering the digitized electrical signals, and wherein said means for determining a spectral content includes means for performing a discrete Fourier transform calculation on the digitized electrical signals.

14. A system as set forth in claim 12, wherein said detecting means includes means for digitizing the electrical signals and means for filtering the digitized electrical signals, and wherein said means for determining a spectral content includes means for performing a power spectral density calculation on the digitized electrical signals.

15. A system as set forth in claim 12, wherein said means for detecting includes an envelope detector for detecting a time (t1) that each contraction begins and a time (t2) that each contraction terminates.

16. A system for detecting an onset of true labor in a pregnant mammal, comprising:

means for detecting electrical signals from a succession of muscular contractions associated with labor; p1 means for determining a spectral content of the electrical signals for each contraction;

means for determining a discriminant (δ) from the determined spectral content for each contraction so as to provide a set of discriminants, individual ones of the set of discriminants being associated with an individual one of the contractions; and means for indicating a beginning of true labor when a slope of at least two discriminants of the set of discriminants exceeds a first threshold value and when a magnitude of a last determined discriminant exceeds a second threshold value, wherein said means for determining a discriminant determines the discriminant in accordance with the expression:

$$\delta=\rho H_\alpha+\sigma H_\beta+\tau H_\gamma+\phi H_\epsilon,$$

where $H_\alpha$, $H_\beta$, $H_\gamma$ and $H_\epsilon$ represent the spectral energy in a plurality of different frequency ranges, and where ρ, σ, τ and φ are constants selected so that δ has a negative value for false labor contractions, and a positive value for true labor contractions.

17. A system as set forth in claim 16, wherein the plurality of different frequency ranges are within a band of frequencies from about 0.1 Hz to about 5.0 Hz.

18. A system as set forth in claim 16, wherein $\alpha$=0.1–1.25 Hz; $\beta$=1.25–2.5 Hz; $\gamma$=2.5–3.75 Hz; and $\epsilon$=3.75–5 Hz.

19. A system as set forth in claim 12, and further comprising:

means for digitizing the detected electrical signals; and means for storing the digitized electrical signals; and wherein said means for indicating is further comprised of means for transmitting at least the stored, digitized electrical signals to a remote location.

20. A system as set forth in claim 19, wherein said system is adapted to be carried by the pregnant mammal, and further comprising, at the remote location, a practitioner's console comprising:

means for receiving and storing the transmitted digitized electrical signals; and means for processing the received and stored digitized electrical signals.

21. A system as set forth in claim 20, wherein said processing means is comprised of:

second means for determining a spectral content of the electrical signals for each contraction;

second means for determining a discriminant (δ) from the determined spectral content for each contraction so as to provide a second set of discriminants, individual ones of the second set of discriminants being associated with an individual one of the contractions; and second means for indicating a beginning of true labor when a slope of at least two discriminants of the second set of discriminants exceeds a first threshold value and when a magnitude of a last determined discriminant exceeds a second threshold value.

22. A system as set forth in claim 12, wherein said detecting means includes means for digitizing the electrical signals and means for filtering the digitized electrical signals, and further comprising means for displaying the filtered digitized electrical signals.

23. A system as set forth in claim 12, and further comprising display means having an input coupled to an output of said determining means for displaying at least one determined discriminant.

24. A system as set forth in claim 12, wherein said indicating means includes means for generating at least one of a visual and an aural indicator.

25. A system as set forth in claim 12, wherein said detecting means includes a set of electrodes that are coupled to the pregnant mammal.

26. A system as set forth in claim 12, wherein said detecting means includes a set of electrodes that are capacitively coupled to the pregnant mammal.

27. A system as set forth in claim 12, wherein said detecting means includes:

means for digitizing the electrical signals;

means for filtering the digitized electrical signals; and means for detecting a time (t1) that each contraction begins and a time (t2) that each contraction terminates; and further comprising memory means for storing filtered digitized electrical signals that occur between time t1 and time t2.

28. A system as set forth in claim 12, wherein said detecting means includes:

means for digitizing the electrical signals;

means for filtering the digitized electrical signals; and means for detecting a time (t1) that each contraction begins and a time (t2) that each contraction terminates; wherein said means for determining a spectral content operates incrementally on said filtered digitized electrical signals; wherein said system further comprising means for summing and integrating said incrementally determined spectral content; and wherein said means for determining a discriminant operates on said summed and integrated incrementally determined spectral content.

29. A method for detecting an onset of true labor in a pregnant mammal, comprising the steps of:

detecting electrical signals from a succession of muscular contractions associated with labor;

determining a spectral content of the electrical signals for each contraction;

determining a discriminant (δ) from the determined spectral content for each contraction so as to provide a set of discriminants, individual ones of the set of discriminants being associated with an individual one of the contractions; and indicating a beginning of true labor when a value of a critical determinant exceeds a threshold value, the value of the critical determinant being obtained from a combination of the slope of at least two discriminants of the set of discriminants and a magnitude of a last determined discriminant.

30. A method for detecting an onset of true labor in a pregnant mammal, comprising the steps of:

detecting electrical signals from a succession of muscular contractions associated with labor;

determining a spectral content of the electrical signals for each contraction;

determining a discriminant (δ) from the determined spectral content for each contraction so as to provide a set of discriminants, individual ones of the set of discriminants being associated with an individual one of the contractions; and indicating a beginning of true labor when a value of a critical determinant exceeds a threshold value, the value of the critical determinant being obtained from a combination of the slope of at least two discriminants of the set of discriminants and a magnitude of a last determined discriminant, wherein the step of determining a discriminant determines the discriminant in accordance with the expression:

$$\delta=\rho H_{\alpha}+\sigma H_{\beta}+\tau H_{\gamma}+\phi H_{\epsilon},$$

where $H_{\alpha}$, $H_{\beta}$, $H_{\gamma}$ and $H_{\epsilon}$ represent the spectral energy in a plurality of different frequency ranges, and where $\rho$, $\sigma$, $\tau$ and $\phi$ are constants selected so that $\delta$ has a negative value for false labor contractions, and a positive value for true labor contractions.

* * * * *